(12) United States Patent
Mohl (10) Patent No.: US 8,626,316 B2
(45) Date of Patent: Jan. 7, 2014

(54) DEVICE FOR THE INTERMITTENT OCCLUSION OF THE CORONARY SINUS

(75) Inventor: Werner Mohl, Altenmarkt-Thennenberg (AT)

(73) Assignee: Miracor Medical Systems GmbH, Vienna (AT)

( * ) Notice: Subject to any disclaimer, the term of this patent is extended or adjusted under 35 U.S.C. 154(b) by 1024 days.

(21) Appl. No.: 12/454,194

(22) Filed: May 14, 2009

(65) Prior Publication Data

US 2010/0256506 A1 Oct. 7, 2010

(30) Foreign Application Priority Data

Apr. 3, 2009 (AT) .................................. A 535/2009

(51) Int. Cl.
*A61M 25/10* (2013.01)
*A61B 5/0215* (2006.01)
*A61M 1/36* (2006.01)
*A61M 25/00* (2006.01)

(52) U.S. Cl.
CPC ............ *A61M 25/10* (2013.01); *A61B 5/02152* (2013.01); *A61M 2001/3613* (2013.01); *A61M 25/0026* (2013.01)
USPC ........................................ 607/122; 604/96.01

(58) Field of Classification Search
None
See application file for complete search history.

(56) References Cited

U.S. PATENT DOCUMENTS

| 1,611,914 | A | 12/1926 | Jenkins |
|---|---|---|---|
| 3,995,623 | A | 12/1976 | Blake et al. |
| 4,589,869 | A | 5/1986 | Wernborg |
| 4,657,536 | A | 4/1987 | Dorman |
| 4,670,009 | A | 6/1987 | Bullock |
| 4,671,796 | A | 6/1987 | Groshong et al. |
| 4,701,166 | A | 10/1987 | Groshong et al. |
| 4,705,501 | A | 11/1987 | Wigness et al. |
| 4,887,608 | A | 12/1989 | Mohl et al. |
| 4,931,036 | A | 6/1990 | Kanai et al. |
| 4,934,996 | A | 6/1990 | Mohl et al. |
| 4,943,277 | A | 7/1990 | Bolling |
| 4,969,470 | A | 11/1990 | Mohl et al. |
| 5,021,045 | A | 6/1991 | Buckberg et al. |
| 5,024,668 | A | 6/1991 | Peters et al. |
| 5,156,600 | A | 10/1992 | Young |
| 5,224,938 | A | 7/1993 | Fenton, Jr. |
| 5,226,427 | A | 7/1993 | Buckberg et al. |
| 5,275,169 | A | 1/1994 | Afromowitz et al. |
| 5,324,260 | A | 6/1994 | O'Neill et al. |
| 5,456,665 | A | 10/1995 | Postell et al. |
| 5,458,574 | A | 10/1995 | Machold et al. |
| 5,466,216 | A | 11/1995 | Brown et al. |
| 5,486,192 | A | 1/1996 | Walinsky et al. |
| 5,505,698 | A | 4/1996 | Booth et al. |
| 5,533,957 | A | 7/1996 | Aldea |
| 5,683,347 | A | 11/1997 | Miyata et al. |
| 5,707,358 | A | 1/1998 | Wright |
| 5,755,686 | A | 5/1998 | O'Neill et al. |
| 5,775,327 | A | 7/1998 | Randolph et al. |
| 5,779,685 | A | 7/1998 | Thompson et al. |
| 6,029,671 | A | 2/2000 | Stevens et al. |
| 6,090,096 | A | 7/2000 | St. Goar et al. |
| 6,179,815 | B1 | 1/2001 | Foote |
| 6,179,856 | B1 | 1/2001 | Barbere |
| 6,475,209 | B1 | 11/2002 | Larson et al. |
| 6,500,145 | B1 | 12/2002 | Bicakci et al. |
| 6,506,146 | B1 | 1/2003 | Mohl et al. |
| 6,508,777 | B1 | 1/2003 | Macoviak et al. |
| 6,569,145 | B1 | 5/2003 | Shmulewitz et al. |
| 6,673,040 | B1 | 1/2004 | Samson et al. |
| 6,758,854 | B1 | 7/2004 | Butler et al. |
| 6,860,876 | B2 | 3/2005 | Chen |
| 7,166,100 | B2 | 1/2007 | Jordan et al. |
| 7,331,922 | B2 | 2/2008 | Mohl |
| 2001/0011161 | A1* | 8/2001 | Edwards et al. ................. 604/22 |
| 2001/0020160 | A1 | 9/2001 | Esch et al. |
| 2001/0041863 | A1 | 11/2001 | Sweezer |
| 2001/0053920 | A1 | 12/2001 | Shaker |
| 2002/0035361 | A1* | 3/2002 | Houser et al. ................... 606/15 |
| 2002/0072730 | A1 | 6/2002 | McGill et al. |
| 2002/0120232 | A1 | 8/2002 | Stumpp et al. |
| 2003/0032974 | A1 | 2/2003 | Leschinsky et al. |
| 2004/0172004 | A1 | 9/2004 | Mohl |
| 2005/0015048 | A1* | 1/2005 | Chiu et al. ............... 604/101.04 |
| 2005/0124849 | A1* | 6/2005 | Barbut et al. .................... 600/18 |
| 2005/0182330 | A1* | 8/2005 | Brockway et al. ............ 600/486 |

(Continued)

FOREIGN PATENT DOCUMENTS

| AT | 503787 B1 | 1/2008 |
|---|---|---|
| EP | 0 230 996 | 8/1987 |

(Continued)

OTHER PUBLICATIONS

Austrian Search Report, dated Nov. 6, 2009, 3 pages.

(Continued)

*Primary Examiner* — Frederick Krass
*Assistant Examiner* — Isaac Shomer
(74) *Attorney, Agent, or Firm* — Fish & Richardson P.C.

(57) ABSTRACT

In a device for the intermittent occlusion of the coronary sinus, including a catheter with several lumens, an occlusion device fixed to the catheter and operable through at least one lumen of the catheter, and at least one pressure measuring device for measuring the fluid pressure in the coronary sinus, the catheter additionally comprises support means for supporting the catheter on the inner wall of the coronary sinus, which support means are reversibly placeable in abutment on the inner wall of the coronary sinus by an operating element.

19 Claims, 5 Drawing Sheets

(56) References Cited

U.S. PATENT DOCUMENTS

| | | | |
|---|---|---|---|
| 2006/0074399 A1 | 4/2006 | Bates | |
| 2006/0100639 A1 | 5/2006 | Levin et al. | |
| 2007/0060883 A1 | 3/2007 | Doty | |
| 2007/0083126 A1 | 4/2007 | Marko et al. | |
| 2007/0123925 A1* | 5/2007 | Benjamin et al. | 606/194 |
| 2008/0015404 A1* | 1/2008 | Mohl | 600/16 |
| 2008/0119742 A1 | 5/2008 | Mohl | |
| 2010/0056849 A1 | 3/2010 | Mohl | |
| 2010/0130810 A1 | 5/2010 | Mohl | |

FOREIGN PATENT DOCUMENTS

| | | |
|---|---|---|
| EP | 1 611 914 | 1/2006 |
| UA | 14911 U | 6/2006 |
| WO | wo 89/10155 | 11/1989 |
| WO | WO 03/008018 | 1/2003 |
| WO | WO 03/041783 | 5/2003 |

OTHER PUBLICATIONS

Mohl, Werner et al. "Coronary Sinus Library, ICSO and PICSO" Society of Coronary Sinus Interventions, 2003. A. Holzhausens Nfg., Austria.

'Cannulation' [online]. Medtronic, Inc. 2010 [retrieved May 27, 2010]. Retrieved from the Internet: <URL: http://www.medtronic.com/for-healthcare-professionals/products-therapies/cardiovascular/therapies/cannulation/index.htm>.

'Cardioplegia Delivery' [online]. Quest Medical, Inc. 2010 [retrieved May 27, 2010]. Retrieved from the Internet: <URL: http://www.questmedical.com/products/cardio_catheters.asp>.

'Global Myocardial Protection' [online]. Edwards Lifesciences, 2004 [retrieved May 27, 2010]. Retrieved from the Internet: <URL: http://ht.edwards.com/resourcegallery/products/cannulae/images/ar00519.pdf>.

'Letters to the Editor: A New Technique for Pulmonary Arterial Catheter Insertion into Coronary Sinus Using Transesophageal Echocardiography' [online]. International Anesthesia Research Society, 2003 [retrieved May 27, 2010]. Retrieved from the Internet: <URL: http://www.anesthesia-analgesia.org/content/97/1/298.full.pdf>.

'MiRCSP Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/mircsp-cannula/index.htm>.

'Myocardial Protection System' [Online]. Quest Medical, Inc. 2010 [retrieved May 27, 2010]. Retrieved from the Internet: <URL: http://www.questmedical.com/products/mps.asp>.

'Performer CPB' [online]. Medtronic, Inc. 2007 [retrieved May 27, 2010]. Retrieved from the Internet: <URL: http://medtronic.com/cardsurgery/arrested_heart/downloads/200704933.pdf>.

'Retrograde Perfusion Cannulae' [online]. Medtronic, Inc. 2010 [retrieved May 27, 2010]. Retrieved from the Internet: <URL: http://www.medtronic.com/for-healthcare-professionals/products-therapies/cardiovascular/cannulae-products/retrograde-perfersion-cannulae/index.htm>.

Mohl, Werner et al., "Is activation of coronary venous cells the key to cardiac regeneration?" Macmillan Publishers Ltd., 2008. Nature Clinical Practice, Cardiovascular Medicine, vol. 5, No. 9, pp. 528-530.

Mohl, Werner et al., "The legacy of coronary sinus interventions: Endogenous cardioprotection and regeneration beyond stem cell research." The American Association for Thoracic Surgery, 2008. The Journal of Thoracic and Cardiovascular Surgery, vol. 136, No. 5, pp. 1131-1135.

Onorati et al., "Coronary Sinus Perfusion Reverses Ongoing Myocardial Damage in Acute Ischemia." Wiley Periodicals, Inc. 2009. Journal compilation, International Center for Artificial Organs and Transplantation and Wiley Periodicals, Inc., 33 (10), pp. 788-797.

Mohl et al., "Intermittent pressure elevation of the coronary venous system as a method to protect ischemic myocardium," *Interact CardioVac Thorac Surg.*, 2005, 4:66-69.

Syeda et al., "The salvage potential of coronary sinus interventions: Meta-analysis and pathophysiologic consequences," *J Thorac Cardiovasc Surg.*, 2004, 124:1703-1712.

\* cited by examiner

DEVICE FOR THE INTERMITTENT OCCLUSION OF THE CORONARY SINUS

CROSS-REFERENCE TO RELATED APPLICATION(S)

Priority is claimed to Austria Pat. App. A535/2009, filed Apr. 3, 2009, hereby incorporated by reference.

TECHNICAL FIELD

The invention relates to a device for the intermittent occlusion of the coronary sinus, including a catheter with several lumens, an occlusion device fixed to the catheter and operable through at least one lumen of the catheter, and at least one pressure measuring device for measuring the fluid pressure in the coronary sinus.

BACKGROUND

Arterial blood, which supplies the heart muscle, is able to pass through healthy heart tissue while nourishing the same, yet has difficulty reaching ischemic tissue. As a result, the supply of ischemic tissue with nutrients and the discharge of metabolic catabolites from such ischemic tissue will be impaired.

In this context, it has already been proposed to supply the ischemic tissue with blood through retrograde perfusion. To this end, it has already been proposed to use an inflatable balloon fixed to the end of a catheter to intermittently occlude the coronary sinus. The blood pressure in the coronary sinus rises during the occlusion at every heart beat so as to cause blood reaching the coronary sinus through the healthy tissue of the heart muscle to be flushed back into the ischemic tissue. For such an intermittent coronary sinus occlusion, the balloon end of the catheter is inserted either percutaneously or surgically. The other end of the catheter is supplied with a gas or fluid by a pump, which causes the cyclic inflation and deflation of the balloon.

A device for the retroinfusion of coronary veins is, for instance, known from WO 2005/120602, by which a pressure-controlled, intermittent coronary sinus occlusion can be performed. In that device and the associated method for determining the optimum times for triggering and releasing the occlusion, pressure parameters like the speeds of the pressure increase and pressure drop were determined and subjected to relatively complex processing. That previously known device, however, involved the drawback that, at a release of the occlusion, the catheter and, in particular, the free end of the catheter was no longer guided in the coronary sinus, as would be the case if the balloon were inflated. As a result, the catheter was able to move freely within the vessel upon release of the occlusion, thus causing the pressure measuring devices, which are usually arranged in the end region of the catheter, to deliver imprecise measuring data at a contact of the vessel wall and a number of artefacts to negatively influence the data determined for calculating the occlusion times. The thus determined data of minor quality subsequently rendered difficult the precise and reproducible determination of the times suitable as occlusion start and end points.

SUMMARY

It is, therefore, the object of the present invention to further develop a device of the initially defined kind to the effect that the pressure measuring device, which is arranged on the catheter, will remain positioned in the center of the vessel even upon release of the occlusion, such that any contacting of the inner wall of the coronary sinus by the pressure measuring device will be excluded.

To solve this object, a device of the initially defined kind according to the invention is further developed to the effect that the catheter additionally comprises support means for supporting the catheter on the inner wall of the coronary sinus, which support means are reversibly placeable in abutment on the inner wall of the coronary sinus by an operating element. Support means separate from the occlusion device are thus provided to keep away from the vessel walls the catheter and the pressure measuring device arranged thereon, even if the occlusion device, which may, for instance, be designed as a conventional balloon, does not abut on the vessel walls. The pressure measuring devices, which are usually comprised of catheter wall apertures communicating with lumens in the interior of the catheter, through which lumens the pressure prevailing in the coronary sinus is, in turn, applied to sensors, are kept away from the vessel walls by said separate support means irrespectively of the occlusion device such that the highly sensitive sensors will not be interfered with by the apertures of the pressure measuring devices contacting the vessel wall.

Another advantage of the present invention resides in that the abutment of the support means on the inner wall of the coronary sinus also allows the catheter to be secured against displacement in the longitudinal direction of the coronary sinus, which will frequently occur if the pressure in the vessel increases as a result of the occlusion.

Principally suitable as support means are any mechanical devices which are tightly arranged on the catheter, or integrated in the latter, for the introduction of the catheter and which, for support on the inner wall of the coronary sinus, are able to enlarge their diameters, or can be brought into a position protruding from the catheter, so as to ensure a defined distance of the catheter from the vessel walls. In this respect, it is essential that the support means do not impede the drainage of the impounded blood after the release of the occlusion, to which end the support means have to include, or leave free, a plurality of passage openings. In a simple manner, the invention is further developed to the effect that the support means are comprised of a basket-like or cage-like structure which is expandable in the radial direction, wherein at least one end of the basket-like or cage-like structure is fixed to a catheter portion which is displaceable relative to a further catheter portion. A basket-like or cage-like structure in the sense of the present invention is meant to denote, for instance, filamentous structures or structures comprising elongate plates, which may be made of metal and/or synthetic materials. Such a basket-like or cage-like structure may, in particular, be comprised of a tubular braid which can be spread apart by the two relatively displaceable catheter portions.

To realize a particularly simple and compact construction of a device according to the invention, the invention is advantageously further developed to the effect that the support means are comprised of an expandable basket-like or cage-like structure whose two ends are fixed to catheter portions which are relatively displaceable in the axial direction. A relative displacement of the two portions which are relatively displaceable in the axial direction causes the basket-like or cage-like structure to be compressed in the axial direction, which will bring about an increase in its diameter in the radial direction and allow the achievement of a firm abutment on the vessel wall. As the two relatively displaceable portions are being returned into their starting positions, the basket-like or cage-like structure is again extended to subsequently abut on the catheter again and, hence, enable the removal of the catheter from the blood vessel.

An embodiment in which the essential functional components of the catheter are arranged in a closely limited longitudinal region of the catheter, and by which optimum measuring results will be achieved, is provided according to a preferred further development of the present invention in that the occlusion device is arranged radially within the expandable basket-like or cage-like structure. In this case, the basket-like or cage-like structure surrounds the occlusion device, for instance a balloon, wherein the apertures of the pressure measuring devices are arranged in a distal relationship relative to the occlusion device. This embodiment, moreover, offers the advantage that, in case the balloon is expanded and, hence, in abutment on the vessel walls of the coronary sinus, the support means, which may, for instance, be comprised of a metallic braid, will be relatively firmly pressed at the vessel wall such that a relatively strong frictional engagement will result and the catheter will be prevented from being pressed out of the coronary sinus by the fluid pressure of the impounded blood.

An alternative embodiment of the device according to the invention, in which the catheter can be fixed to the inner wall of the coronary sinus for supporting purposes, according to a preferred further development of the present invention can be realized in that the support means are formed by a catheter portion which is helically deformable by a cable pull of the catheter. The cable pull, which may, for instance, extend in the interior of the catheter in the form of a Bowden cable pull, upon actuation will subject the catheter to compressive stress such that, with the appropriate choice of materials in the deformable region of the catheter, the latter will be deformed into helical configuration. The diameter of the resulting twisted shape is naturally larger than the diameter of the catheter, so that the deformed region of the catheter will come into abutment on the inner wall of the coronary sinus. The pressure measuring devices in this case are arranged outside the deformable region so as to again be in a safely distanced relationship relative to the vessel wall with the support means in abutment on the vessel wall.

The device according to the invention is advantageously further developed to the effect that the catheter portion carrying the pressure measuring device, with the support means in abutment on the inner wall of the coronary sinus, is radially arranged substantially centrally between the points of abutment of the support means on the inner wall of the coronary sinus, whereby the apertures of the pressure measuring devices are arranged at regular distances from the vessel walls such that even apertures arranged in different peripheral sections for pressure measuring devices will provide reproducible results.

In order to enable the observation of the support means during the insertion of the catheter and the establishment of the abutment of the support means on the inner wall of the coronary sinus, the device according to the invention is advantageously further developed to the effect that the support means comprise a radiopaque or echogenic coating. Such coating enables the angiographic or ultrasonic observation of the expansion of the support means and the visual pursuit of the abutment of the support means on the inner wall of the coronary sinus. This will ensure enhanced ease of operation to the surgeon and improve safety for the patient, since injuries of the vessel wall by excessive abutment forces will be prevented.

According to a preferred embodiment of the present invention, the device for the intermittent occlusion of the coronary sinus is further developed to the effect that the occlusion device comprises at least one electrically conductive region adapted to be contacted by an electrically conductive region provided on the support means. The at least one electrically conductive region may, for instance, be contacted by the support means when the occlusion means, for instance a balloon, is completely expanded and, thus, abuts the support means. In this manner, an electrical contact can be closed, which allows the subsequent detection that the occlusion device completely occludes, so as to prevent excessive filling of the balloon and, hence, an excessive dilatation of the vessel.

In order to enable the monitoring of the depth of insertion of the catheter into the vessel system and, in particular, the position of the catheter within the coronary sinus by the above-mentioned imaging methods, the device according to the invention is preferably further developed to the effect that the catheter comprises a plurality of radiopaque or echogenic markings, which markings may be provided at regular distances on the catheter and, in particular, in the end region and in the region of the occlusion device.

In order to enable the simple establishment of the abutment of the support means on the inner wall of the coronary sinus in the described manner, by a relative displacement of movable parts or by the operation of a cable pull, the invention is advantageously further developed to the effect that a handle is connected with the relatively displaceable catheter portions or with the cable pull, respectively, so as to enable the surgeon to secure the position of the catheter within the coronary sinus by one hand and establish the abutment of the support means on the inner wall of the coronary sinus by operating the handle with the other hand.

The introduction of the catheter into the coronary sinus requires considerable skill from the surgeon, while avoiding that interfering parts project from the otherwise smooth structure of the catheter. In order to prevent any unintentional expansion of the support means, the device according to the present invention is advantageously further developed to the effect that the catheter comprises a sheathing hose which can be sleeved over the support means when the latter are not in abutment on the inner wall of the coronary sinus. During the introduction of the catheter into, or extraction of same out of, the vessel system, the sheathing hose will cover the support means and can only be retracted immediately before the support means are brought into abutment on the inner wall of the coronary sinus.

An indicator for the success of treatment is the blood volume stream in the non-occluded coronary sinus. In order to be able to measure the same during treatment, the device according to the present invention is advantageously further developed to the effect that an ultrasonic measuring device for the blood volume stream is arranged in the coronary sinus. Such device are comprised of transmitter elements including crystals emitting ultrasonic waves and the respective receiver elements, with the propagation times between the transmitter and receiver elements in the flow direction and opposite the flow direction depending, inter alia, on the volume stream. The volume stream can be computationally determined from the difference of the propagation times.

DESCRIPTION OF DRAWINGS

In the following, the invention will be explained in more detail by way of an exemplary embodiment schematically illustrated in the drawing. Therein.

DESCRIPTION

Figure 1:
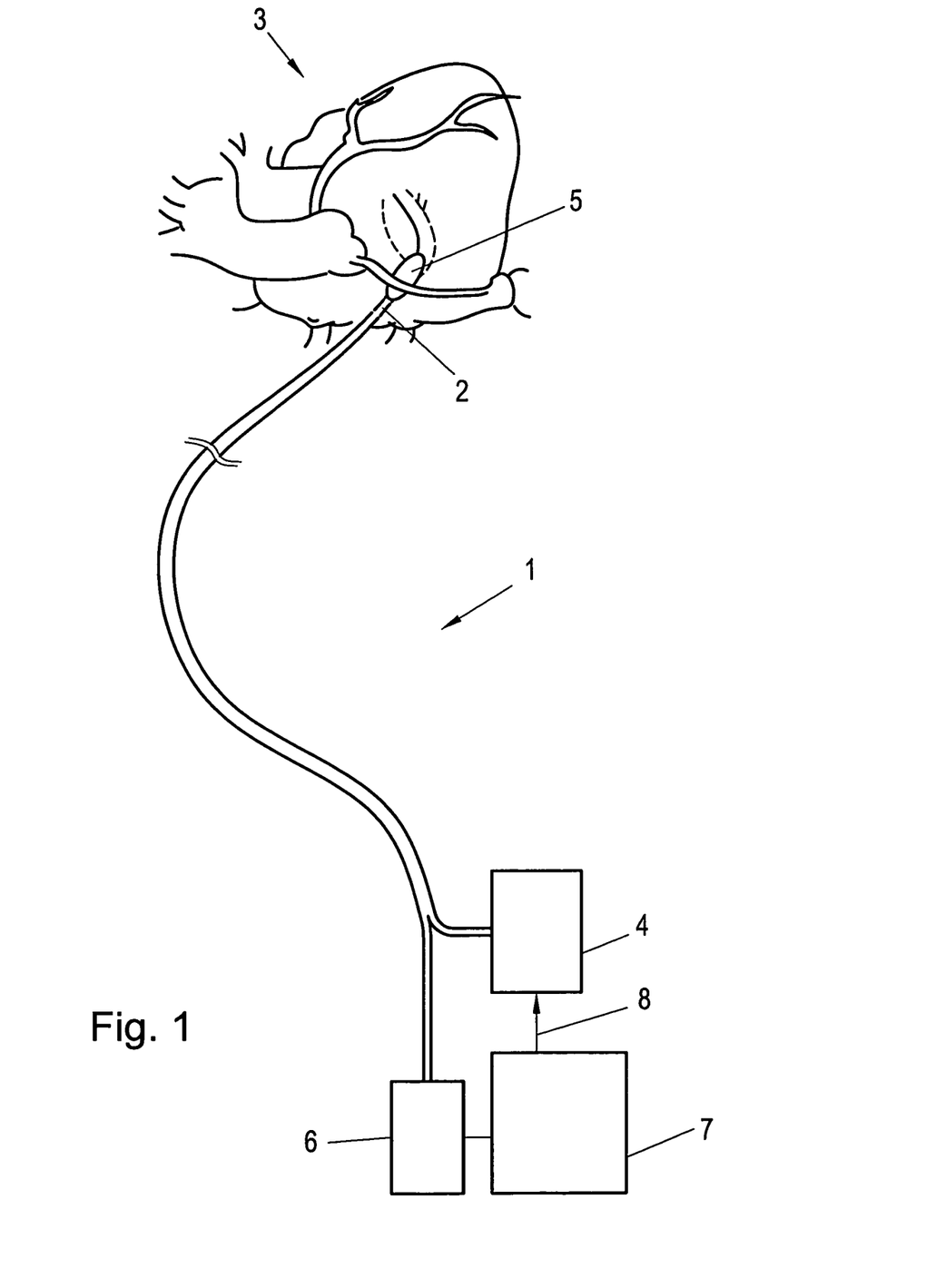
FIG. 1 is a schematic view of a heart comprising a device for the intermittent occlusion of the coronary sinus according to the present invention.

In FIG. 1, the device for the intermittent occlusion of the coronary sinus is schematically denoted by 1, wherein a multi-lumen catheter 2 is apparent, whose distal end is inserted in the coronary sinus of the heart 3 via the atrium. One lumen of the catheter 2 is connected with a pump 4, which provides pressure medium for inflating the occlusion device 5. The pressure in the coronary sinus is acquired by a pressure measuring device 6, said pressure measuring device 6 also including a memory for the detected measurements. The respectively measured pressure values are fed to a control device comprising an evaluation circuit 7 to deliver control signals via line 8 for starting and stopping the pump 4.

Figure 2:
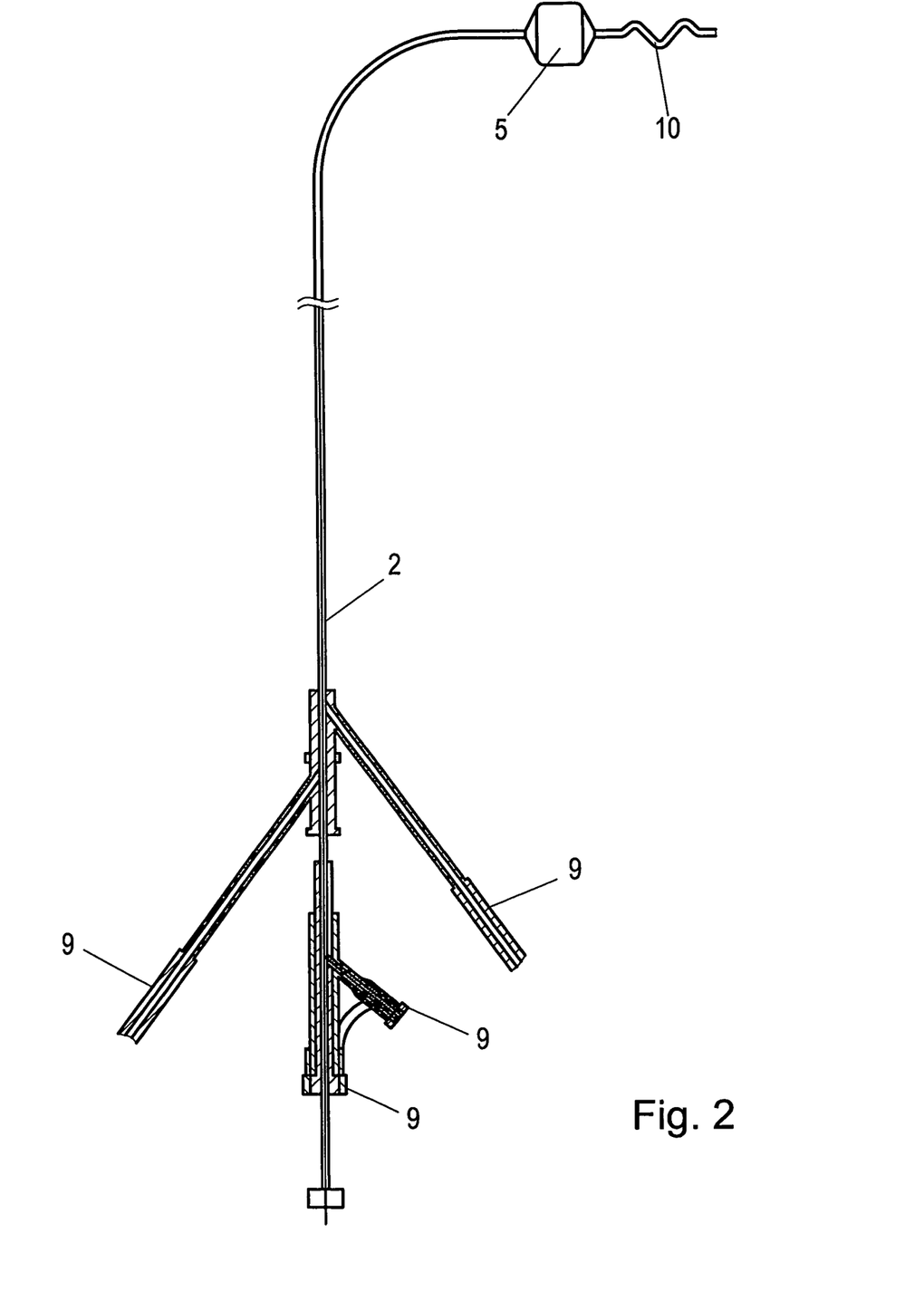
FIG. 2 is an overall view of a catheter according to the invention.

In FIG. 2, the catheter is again denoted by 2, wherein pressure medium can be fed to the lumens via connections 9, or mechanical components can be introduced into the catheter through said lumens, via which also pressures from the coronary sinus can be transmitted to sensors. The catheter 2 further comprises an occlusion device 5 in the form of a balloon. Support means 10 are arranged on the distal end of the balloon to support the catheter on the inner wall of the coronary sinus.

Figure 3:
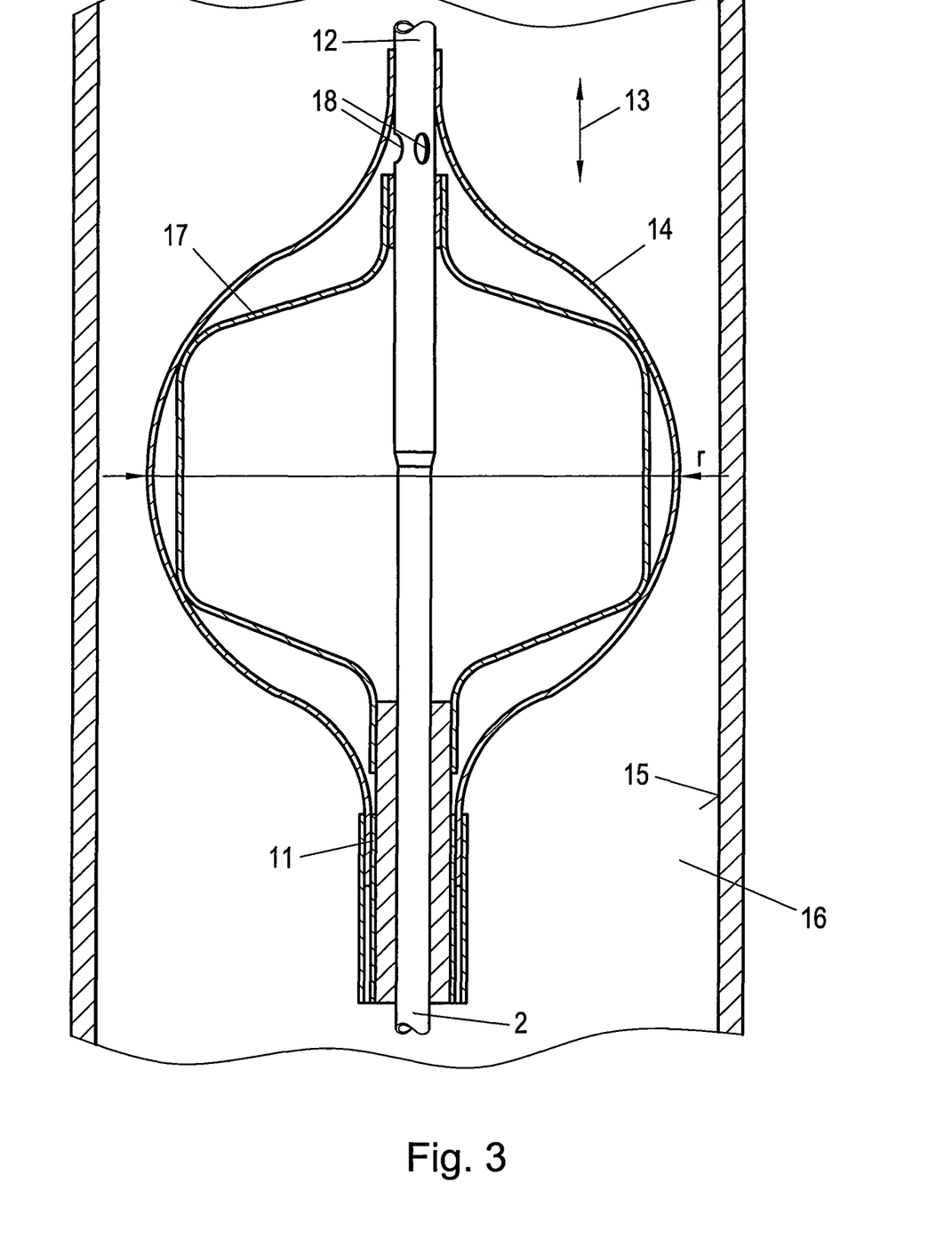
FIG. 3 is a detailed illustration of a device according to the invention, in which the occlusion device is arranged radially within the expandable support means.

From FIG. 3 it is apparent that the catheter 2 is constructed by layers. In a flexible tube 11, a further tube 12 is guided, said tubes 11 and 12 being relatively displaceable along double arrow 13. A cage-like structure 14 is fixed to the tubes 11 and 12. The cage-like structure 14 in this exemplary embodiment is designed as a tubular metallic braid, which is compressed by a relative displacement of the two tubes 11 and 12 along double arrow 13 in such a manner as to increase the radius r and allow the structure 14 to come into abutment on the inner wall 15 of the coronary sinus 16. This effects the centering of the catheter 2 within the coronary sinus 16 irrespectively of the condition of the balloon 17, which can be filled with pressure medium via the catheter 2 for occlusion. Apertures of a pressure measuring device are denoted by 18, which, due to the abutment of the structure 14 on the inner wall 15 of the coronary sinus 16, will be centeredly held within the coronary sinus 16 even if the balloon has collapsed, so as to enable the precise measuring of the fluid pressure in the coronary sinus 16 irrespectively of the condition of the balloon.

Figure 4:
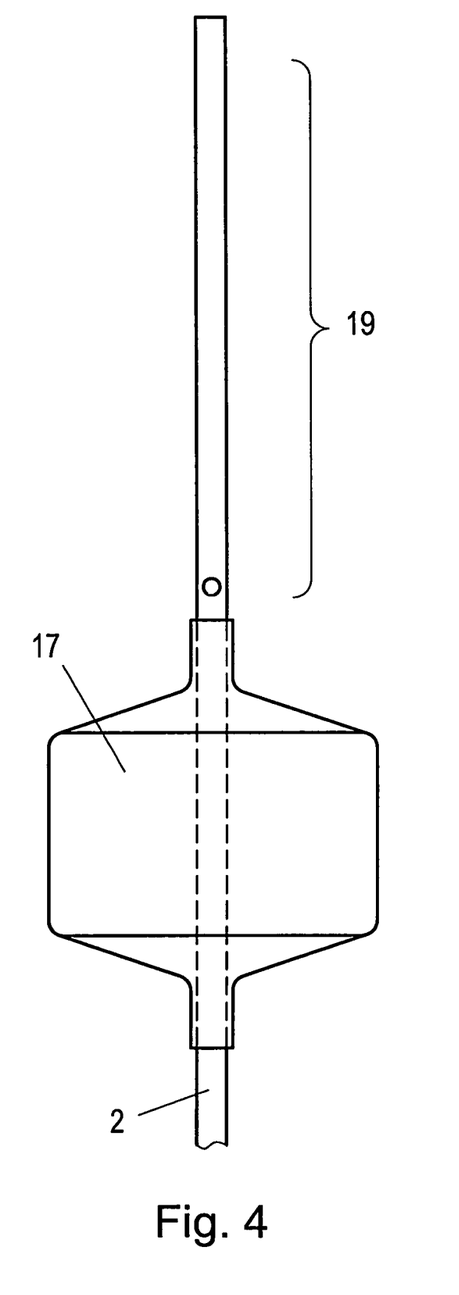
FIGS. 4 and 5 each show alternative embodiments of the present invention, in which the catheter is helically deformable.
Figure 5:
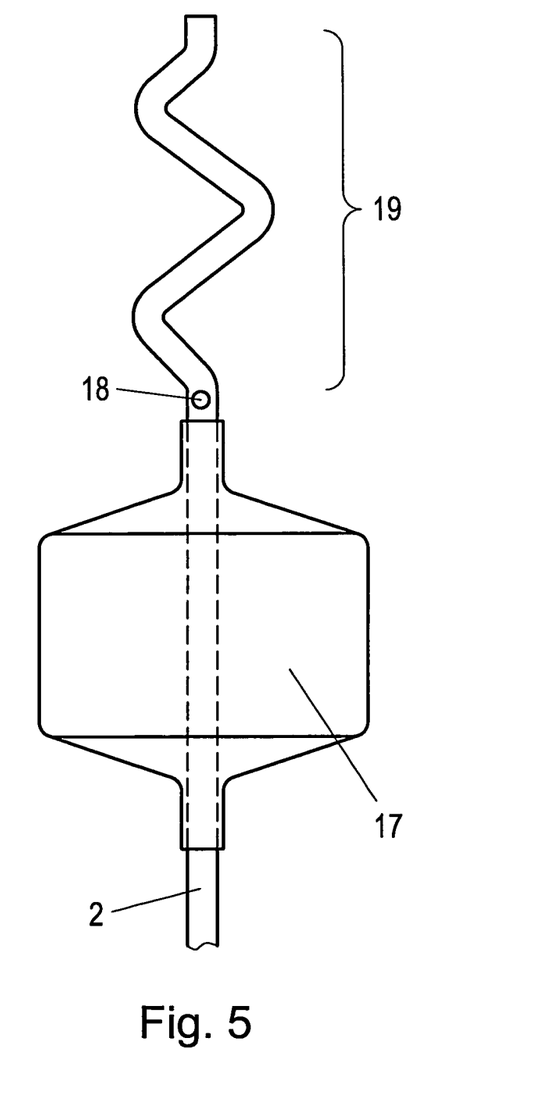

In FIG. 4, the catheter is again denoted by 2, wherein, according to an alternative embodiment of the invention, a deformable portion 19 of the catheter 2 is arranged distally of the balloon 17. The deformable portion 19 can be set under compressive stress by actuating a cable pull not illustrated in detail so as to cause the deformable portion 19 to assume a helical configuration as illustrated in FIG. 5, thus increasing the overall diameter of the end region of the catheter 2. In this manner, the catheter 2 is able to come into abutment on the inner wall of the coronary sinus in the deformable portion 19, so that the apertures 18 of a pressure measuring device will remain centered in the vessel even with the collapsed balloon 17, and artefacts will be avoided during pressure measuring.

Figure 6:
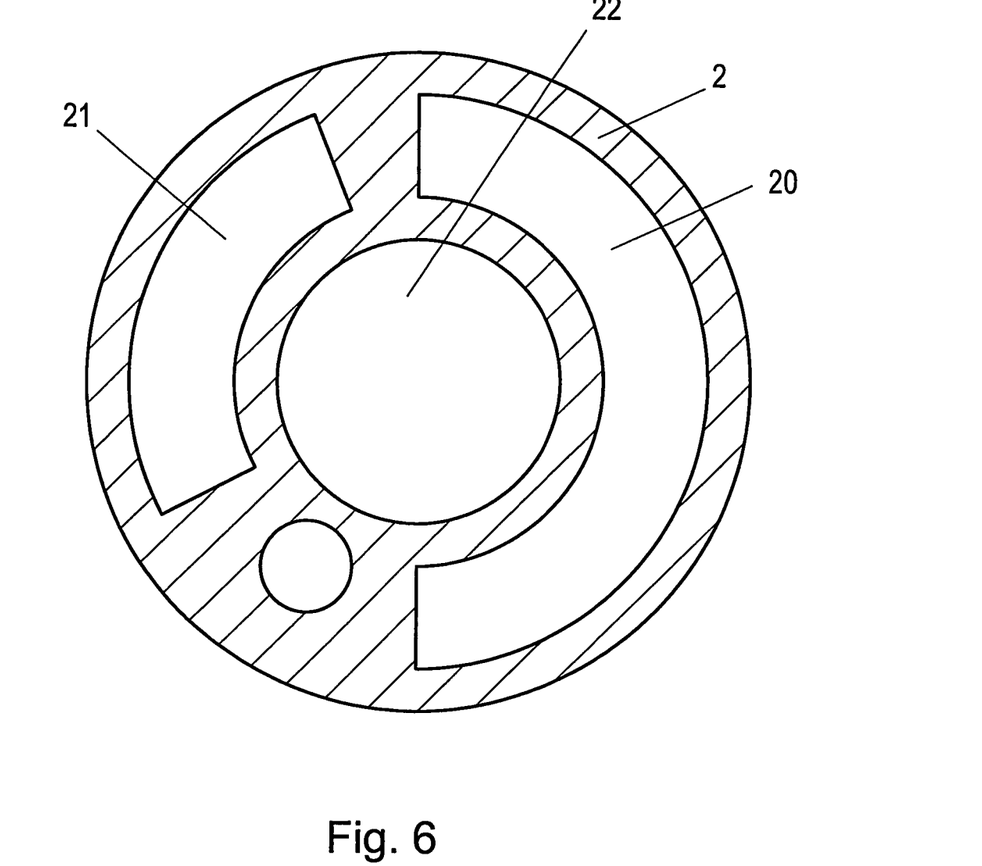
FIG. 6 is a sectional illustration of the catheter.

From FIG. 6, it is apparent that the catheter 2 has several lumens. A lumen via which the balloon, which serves as occlusion device, can be filled with pressure medium is denoted by 20. The extraction of the pressure medium to deflate the balloon is likewise effected via lumen 20. A lumen via which the pressure prevailing in the balloon can be measured is denoted by 21. Lumen 22 is that lumen which, together with the apertures 18 and a pressure sensor, forms the pressure measuring device for the fluid pressure in the coronary sinus. Due to the catheter 2 being centered by the support means 5, pressure waves and artefacts resulting, for instance, from an unsupported catheter hitting at the vessel wall will be prevented, thus allowing a precise measurement of the fluid pressure in the occluded vessel independently of the condition of the occlusion device.

The invention claimed is:

1. A device for intermittent occlusion of a coronary sinus, comprising:
    a catheter comprising a plurality of lumens,
    an occlusion device fixed to the catheter, the occlusion device comprising an inflatable balloon configured to at least partially occlude a coronary sinus of a heart and being in fluid communication with at least one of said lumens of the catheter, and
    at least one pressure measuring device for measuring fluid pressure in the coronary sinus,
    wherein said plurality of lumens of the catheter comprises: a balloon inflation lumen in fluid communication with the inflatable balloon to inflate and deflate the inflatable balloon; a balloon pressure-monitoring lumen to measure fluid pressure in the balloon, the balloon pressure-monitoring lumen being different from and laterally offset from the balloon inflation lumen; a coronary sinus pressure sensor lumen in fluid communication with said pressure measuring device and extending distally of the balloon for communication with fluid in a coronary sinus, the coronary sinus pressure sensor lumen being different from and laterally offset from the balloon inflation lumen and the balloon pressure-monitoring lumen; and a fourth lumen being different from and laterally offset from the balloon inflation lumen, the balloon pressure-monitoring lumen, and the coronary sinus pressure sensor lumen,
    wherein the catheter comprises at least one structure extending distally of a distal end of the inflatable balloon and being reversibly placeable in abutment on an inner wall of the coronary sinus.

2. A device according to claim 1, wherein the at least one structure comprises a support means for supporting the catheter on the inner wall of the coronary sinus.

3. A device according to claim 2, wherein the support means comprises an expandable basket-like or cage-like structure having two ends, and each one of said ends is fixed to one of two catheter portions that are relatively displaceable in an axial direction of the catheter.

4. A device according to claim 1, wherein the occlusion device is arranged radially within a basket-like or cage-like structure.

5. A device according to claim 3, wherein the occlusion device is arranged radially within the basket-like or cage-like structure.

6. A device according to claim 2, wherein the support means comprises a catheter portion that is helically deformable by operation of a cable pull of the catheter.

7. A device according to claim 1, further comprising multiple apertures facing radially outward from the at least one structure, and said multiple apertures being in fluid communication with said coronary sinus pressure sensor lumen and said pressure measuring device.

8. A device according to claim 2, wherein the support means comprises a radiopaque or echogenic coating.

9. A device according to claim 2, wherein the occlusion device comprises at least one electrically conductive region positioned to be contacted by an electrically conductive region positioned on the support means.

10. A device according to claim 1, wherein the catheter comprises a plurality of radiopaque or echogenic markings.

11. A device according to claim 2, wherein a handle is connected with the catheter so as to actuate the support means.

12. A device according to claim 3, wherein a handle is connected with the relatively displaceable catheter portions for displacement of the catheter portions.

13. A device according to claim 6, wherein a handle is connected with the cable pull for operation of the cable pull.

14. A device according to claim 2, wherein the catheter comprises a sheathing hose for sleeving over the support means when the support means is not in abutment on the inner wall of the coronary sinus.

15. A device according to claim 1, further comprising an ultrasonic measuring device for measuring a blood volume stream when the occlusion device is arranged in the coronary sinus.

16. The device according to claim 1, wherein the at plurality of lumens extending through a shaft portion of catheter have cross-sectional geometries differing from one another.

17. The device according to claim 16, wherein the balloon inflation lumen has a ring segment-shaped in cross section and is arranged radially outside the coronary sinus pressure sensor lumen extending centrally through the shaft portion of the catheter.

18. The device according to claim 17, further comprising wherein the balloon pressure-monitoring lumen has a ring segment-shaped in cross section and is arranged offset from the coronary sinus pressure sensor lumen extending centrally through the shaft portion of the catheter, wherein the ring segment-shaped of the balloon pressure-monitoring lumen is smaller as compared to that of the balloon inflation lumen.

19. The device according to claim 1, wherein the at least one structure extending distally of a distal end of the inflatable balloon comprises a catheter tip element in fluid communication with the coronary sinus pressure sensor lumen extending centrally through the shaft portion of the catheter, the catheter tip element defining the multiple apertures that are positioned distally of the inflatable balloon of the occlusion device for communication with fluid in a coronary sinus.

* * * * *